(12) United States Patent
Lehr et al.

(10) Patent No.: US 6,684,094 B1
(45) Date of Patent: Jan. 27, 2004

(54) INSTRUMENT FOR MEDICAL PURPOSES

(76) Inventors: Heinz Lehr, Wiesbadener Strasse 18, D-14197 Berlin (DE); Gerhard Niederfeld, Pfalzburger Strasse 8, D-10719 Berlin (DE)

(*) Notice: Subject to any disclaimer, the term of this patent is extended or adjusted under 35 U.S.C. 154(b) by 0 days.

(21) Appl. No.: 10/009,163

(22) PCT Filed: May 12, 2000

(86) PCT No.: PCT/EP00/04343
§ 371 (c)(1),
(2), (4) Date: Mar. 18, 2002

(87) PCT Pub. No.: WO00/69341
PCT Pub. Date: Nov. 23, 2000

(30) Foreign Application Priority Data

May 14, 1999 (DE) .......................... 199 22 056

(51) Int. Cl.⁷ .............................. A61B 5/05; A61B 8/12
(52) U.S. Cl. ........................................ 600/407; 600/463
(58) Field of Search .................. 600/407, 424, 600/437, 459–471

(56) References Cited

U.S. PATENT DOCUMENTS

| 4,391,282 | A | * | 7/1983 | Ando et al. ............... 600/463 |
| 4,572,201 | A | | 2/1986 | Kondo |
| 4,674,515 | A | | 6/1987 | Andou |
| 4,748,985 | A | | 6/1988 | Nagasaki |
| 4,884,133 | A | | 11/1989 | Kanno |
| 4,936,307 | A | | 6/1990 | Saito |
| 5,240,003 | A | | 8/1993 | Lancee |
| 5,313,950 | A | * | 5/1994 | Ishikawa et al. ........... 600/463 |
| 5,603,327 | A | | 2/1997 | Eberle |

FOREIGN PATENT DOCUMENTS

| DE | 690 25 851 T1 | 6/1996 |
| DE | 196 13 242 A1 | 10/1997 |
| EP | 0 423 895 A1 | 4/1991 |
| JP | 06054848 | 3/1994 |
| JP | 10099326 | 4/1998 |
| WO | WO 90/13253 A1 | 11/1990 |

OTHER PUBLICATIONS

Lehr, et al., "Microactuators as Driving Units for Microrobotic Systems," SPIE, SPIE, p. 202–210, (Apr. 7, 1996).

* cited by examiner

Primary Examiner—Francis J. Jaworski
(74) Attorney, Agent, or Firm—Hahn Loeser + Parks LLP; Stephen L. Grant (57) ABSTRACT

The invention concerns an instrument for medical purposes, comprising a housing (8) which can be introduced into an animal or human body, a movably mounted electromagnetic or acoustic transducer unit (7) arranged in the housing (8), preferably in the distal end thereof, for producing electromagnetic or acoustic waves, in particular ultrasonic waves, and a drive (1, 2) for driving the transducer unit (7), wherein the transducer unit (7) is connected to at least one first contact element (9a) and arranged on the housing (8) is at least one second contact element (8a, 8b; 12a through 12j) provided for sliding contact with the first contact element (9a), wherein the first and second contact elements (9a and 8a, 8b; 12a through 12j) jointly form a radial mounting for the transducer unit (7).

80 Claims, 4 Drawing Sheets

Fig. 9

INSTRUMENT FOR MEDICAL PURPOSES

The invention concerns an instrument for medical purposes, comprising a housing which can be introduced into an animal or human body, a movably mounted electromagnetic or acoustic transducer unit arranged in the housing, preferably in the distal end thereof, for producing electromagnetic or acoustic waves, in particular ultrasonic waves, and a drive for driving the transducer unit, wherein the transducer unit is connected to at least one first contact element and arranged on the housing is at least one second contact element provided for sliding contact with the first contact element.

BACKGROUND OF THE ART

Such instruments can be introduced into the human body or into cavities of the human body, which are accessible from the exterior, in particular for investigative purposes.

To carry out such an investigation of hollow organs and vessels, use is made in medicine inter alia of ultrasonic instruments, by means of which it is possible to obtain information about the structural makeup of biological tissue. By using sound waves, it is possible to observe structures within a piece of tissue, which are frequently only accessible to visual assessment by means of invasive methods. Within the human body however there are numerous cavities between organs and within bones which shield some regions of the body for the external use of ultrasound. Those regions can only be investigated by means of instruments of the kind set forth in the opening part of this specification, preferably ultrasonic instruments, which are to be introduced into the body. In that respect those instruments should be capable of processing sound waves at least in one plane in space so that a sectional representation of the body structure being investigated can be produced from the sound echoes which are received and evaluated by the instruments.

While there is sufficient space available for the scanning operation when using instruments outside the body, the tight conditions in respect of space in the body to be investigated constitute a problem when using instruments which are to be introduced into the body.

Dutch patent application No. 8700632 describes an ultrasonic instrument having a catheter whose tip either contains a rotatably mounted acoustic mirror or a fixed acoustic mirror and is itself mounted rotatably. A flexible shaft which is coupled to the rotatable mirror or the rotatable catheter tip extends from the distal catheter tip to the proximal end of the catheter and is driven by a drive unit disposed outside the catheter. A transducer is mounted in the catheter tip opposite the rotating acoustic mirror. Rotation of the acoustic mirror produces ultrasonic waves in different directions and the echoes of the sound waves are received again by the acoustic mirror and then by the transducer. As the curvature of the flexible shaft within the catheter is not in one plane, bending of the shaft in a plurality of axes relative to the position of the drive unit is also linked to a rotational movement of the transducer. As a result of this and due to static friction effects the directions of the ultrasonic waves cannot be accurately ascertained so that it is not possible to precisely predict how the image represented by the ultrasonic unit is linked to the position of the structure within the human body. The differing amount of friction which the flexible shaft experiences from one revolution to another also results in statistical modulation of the angular speed of the acoustic mirror, which reveals itself as a lack of definition in the image representation of the sound echoes.

To overcome those disadvantages, U.S. Pat. No. 5,603,327 to Eberle No. 5,603,327 proposes subdividing the fixedly installed ultrasonic converter into a plurality of segments, in respect of which the direction of propagation of the sound waves is achieved by suitable actuation control. That however gives rise to the necessity to provide numerous electrical contacting means in a very small space and in addition to integrate amplifiers for pre-amplification of the really weak echo signals from the numerous sound converter segments, into the instrument. That arrangement entails high manufacturing costs. If the instruments are used only once, which is frequently the case, that results in high consumable item costs on the part of the users.

A further possible option involves continuously measuring the position of the ultrasonic converter, whereby correction of the representation is a possibility. That measure is proposed in PCT publication WO 90/13253, assigned to DU-MED B.V. and published Nov. 15, 1990. For that purpose however it is necessary to use an angular measurement converter which however only permits correction of the visualized echoes, which is complicated and expensive in terms of computing power. Unfortunately complete elimination of the described friction effects is also not possible with such an instrument.

A third possible option involves moving the drive which moves the acoustic mirror or sound reflector into the catheter. Such an instrument is disclosed in European Patent Office application 0 423 895 A1, also owned by DU-MED B. V., which constitutes the most relevant state of the art which the present invention takes as its basic starting point. That known arrangement admittedly avoids the disadvantages of the previously described arrangements, but this arrangement only permits the acoustic wave radiation angle to be fixed in a narrow range. It has been found moreover that the structural factors involved with this arrangement means that it is essentially fixed only to high acoustic frequencies.

The object of the present invention is to improve an instrument of the kind set forth in the opening part of this specification, in such a way that it is possible to operate with the highest possible degree of versatility with a transducer unit which is flexible in particular in terms of frequency and radiation direction of the waves.

SUMMARY OF THE INVENTION

That object is attained in that, in an instrument of the kind set forth in the opening part of this specification, the first and second contact elements jointly form an at least radial mounting for the transducer unit.

Such an arrangement makes it possible to provide a transducer unit which is preferably rotatably mounted and which is substantially directly driven by the drive without the transducer unit requiring a large amount of space. In actual fact, the arrangement according to the invention in which the sliding contacts for contacting the transducer unit at the same time provide for radial mounting of the transducer unit and preferably also axial mounting affords a highly compact and at the same time reliable design configuration. A compact structure increases in particular the large number of possible uses of the instrument which in fact is also to be introduced into narrow natural or artificial openings in the body.

This arrangement also makes it easier for the drive and the transducer unit to be integrated in a compact housing. That affords various advantages. A major advantage is that on the one hand an acoustic mirror or sound reflector and on the other hand force-transmitting means such as for example a shaft are not required, which results in a simplified structure and a perceptible reduction in manufacturing costs. The damped elastic mounting for the transducer unit by the sliding contacts and the substantially direct rigid mechanical coupling of the drive and the transducer unit also reduces oscillations as a consequence of friction, which are superimposed on the movement which is predetermined by the drive, while in addition, by virtue of the very uniform movement of the transducer unit which is achieved in that way, that results in very uniform scanning by the waves generated by the transducer unit.

In addition there is a great deal of scope in regard to the design configuration of the transducer unit, in which respect in particular the frequency and the radiation angle can be virtually freely selected. Finally, the compact structure achieved by means of the arrangement according to the invention, which involves all necessary and mechanical components, permits simple assembly and dismantling, which results in inexpensive re-usability of essential components of the instrument.

Preferably the first and second contact elements also form an axial mounting. The axial mounting is preferably afforded by a peripheral groove in the first contact elements, into which engage contact springs of the second contact element. The engagement of the second contact elements into the respective peripheral grooves provides that the first contact elements are axially fixed with respect to the second contact elements without a rotary movement being impeded. In addition however it is also possible to provide other radial and possibly also axial mountings and/or seals which perform that mounting function.

The transducer unit can comprise one or more transducer segments, preferably acoustically operative segments.

A construction which is particularly preferred at the present time is distinguished in that the transducer unit is connected to at least one first contact element, at least one second contact element is arranged on the housing and the first and second contact elements are in mutual sliding contact, thereby affording continuous and reliable contacting and thus reliable electrical connection of the movably supported transducer unit. It will be appreciated that a plurality of first and second contact portions can be provided, in particular if the transducer unit comprises a plurality of transducer segments. In that respect the first and second contact elements each form a respective contact pair of which the second contact element forms the counterpart contact for the first contact element. Usually, at least two contact pairs are required for electrical contacting of the transducer unit so that the number of contact pairs is increased by at least one further contact pair for each segment which is to be freshly added if the transducer unit comprises more than one transducer segment.

The first and/or second contact elements are preferably elastically mounted, which ensures that the contact made is particularly certain. For that purpose it is also possible for the contact elements themselves to be of an elastic nature.

With such a contacting arrangement a plurality of contact elements which are elastically suspended independently of each other and which are electrically connected to each other can simultaneously contact one or more electrically interconnected contact partners which are rigidly connected to each other.

A development of this design configuration, which is particularly preferred at the present time, is distinguished in that the transducer unit is carried on a rotating and/or linearly oscillating shaft which is driven by the drive and on which the first contact elements are arranged. In that case the conductors connecting the first contact elements to the transducer unit can be arranged within the shaft, whereby the conductors are disposed in a particularly space-saving and compact fashion. For that purpose the shafts can be hollow and the conductors can be in the form of mutually insulated wires. For arranging the conductors within the shaft, it is either possible to select a coaxial structure or the conductors can be laid on the surface of an insulating layer applied to the inside surface of the shaft which is in the form of a hollow shaft. Equally the shaft itself can also be used as conductors, whereby it is possible to save on at least one wire, which also has an advantageous effect on manufacturing costs.

Desirably the second contact element is in the form of a spring, in which case the first contact element can be in the form of an annular portion surrounding the shaft and the second contact element can substantially tangentially touch the first contact element in order to achieve reliable contact. For that purpose the second contact element can be in the form of a straight or curved spring plate. Alternatively the second contact element can also be in the form of a coil spring surrounding the shaft, whereby it is possible to achieve a greater spring travel. In that case the cross-section of the movable second contact element can be adapted as desired to the demands of reliable contact-making. In particular square or round cross-sections of the individual contact springs, with a cross-section which is variable over the length thereof, are a possibility.

If the first contact elements are arranged on the shaft of the transducer unit and are contacted by the second contact elements by means of contact springs from the exterior, then the peripheral groove for implementing the axial mounting action is preferably disposed on the outside of the first contact elements.

Alternatively however spring contacts can also be provided on the transducer unit or the shaft thereof, being surrounded by contact sleeves with which they are in engagement. The contact sleeves are preferably arranged on the housing and for axial mounting thereof can have grooves on their internal peripheral surfaces.

The first and second contact elements can be arranged jointly in a first housing portion which is sealed off in relation to the rest of the housing and contains gas or liquid. This arrangement serves essentially for affording sealing integrity in relation to a medium which is used for acoustic coupling of the transducer unit which is in the form of an ultrasonic transducer. In this case neither the gas nor the liquid is to have an adverse effect in respect of the electrical properties, in particular electrical attenuation and insulation of different contact elements relative to each other, nor are the flow properties thereof to result in the contact elements floating up or in an inadmissible increase in the frictional moment.

For direct coupling to the transducer unit the drive should preferably be arranged in the housing, in the direct proximity of the transducer unit.

The drive can have an electrostatic, electromagnetic, piezoelectric, magnetostrictive or fluid motor and for the purposes of increasing torque can be selectively provided with a transmission which has one or more stages and which provides for a uniform or non-uniform step-up effect. It is additionally possible to provide a regulating means which for example can have an angle measurement converter, or a synchronous motor can be used for this purpose.

The transducer unit may optionally have a plurality of transducers, preferably ultrasonic converters, which are oriented axially and/or radially in relation to the longitudinal axis of the housing. In that case each of those transducers may in turn comprise one or more active segments of variable arrangement and shape. The contacting configuration when using a plurality of transducers and/or segments can in that case be such that current paths which are always at the same electrical potential can be combined together and contacted by way of a single contact element pair.

If the transducer unit has at least one ultrasonic converter it can be arranged in a second housing portion which is sealed off with respect to the rest of the housing and contains a fluid for acoustic coupling purposes.

Usually the instrument is provided with a catheter, with the housing being removably fixed to the distal end of the catheter. In that case therefore the housing forms a structural unit for receiving the drive, the contacting means and the transducer unit which can be assembled and dismantled in a simple manner in the form of a functional unit. This together with sterilizability of all components ensures economical re-usability.

Finally the housing can be in the form of a tube, particularly when it is fixed to a catheter.

Further preferred configurations of the invention are set forth in the appendant claims.

BRIEF DESCRIPTION OF THE DRAWINGS

A preferred embodiment of the invention is described in greater detail hereinafter with reference to the accompanying drawings in which.

DETAILED DESCRIPTION OF THE INVENTION

Figure 1:
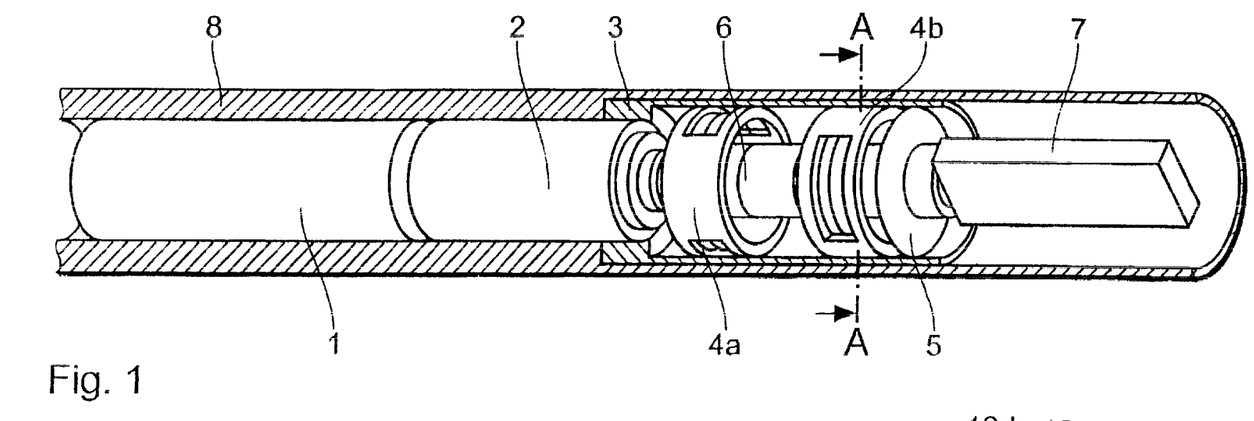
FIG. 1 is a perspective partly sectional view showing the distal end of an ultrasonic instrument.

FIG. 1 shows a configuration by way of example of the distal end of an ultrasonic instrument for uses within the human body.

The distal end has a drive with a motor 1 which can be for example in the form of a synchronous motor which provides a constant rotary speed. In that respect preferably electrostatic, electromagnetic, piezoelectric, magnetostrictive or fluid motors are to be considered. If in particular a different kind of motor from a synchronous motor is used, a drive regulating means should be provided, which operates for example with an angle measurement converter. In the illustrated structure the motor 1 is coupled by way of an output shaft (not shown) to a transmission 2 which is used to increase the amount of torque. In that case it is possible to provide a transmission which has one or more stages and which has a uniform or non-uniform step-up action, with an epicyclic transmission being preferred.

Extending in the axial direction from the output end of the transmission 2 is an inner tubular housing 3 which accommodates two mutually spaced sliding or slip rings 4a and 4b. The slip rings 4a and 4b are each of a cylindrical shape and are disposed with their external peripheral surface in contacting relationship against the inside wall surface of the internal housing 3. As FIG. 1 shows the two slip rings 4a and 4b are arranged at an axial spacing from each other and from the transmission 2.

Coupled to the output of the transmission 2 is a shaft 6 which extends through the two successively arranged slip rings 4a, 4b and which in this case is arranged coaxially in relation to the slip rings and the internal housing 3.

At the free end in opposite relationship to the transmission 2, the tubular internal housing 3 is closed by a sealing ring 5 through which the shaft extends in sealing relationship therewith. Thus the internal housing 3 forms a compartment which is closed with respect to the surrounding environment and whose volume can be filled with a gas or a liquid whose electrical properties however do not have an adverse effect either in regard to dielectric damping or in regard to mutual insulation of the contacts of the two slip rings 4a and 4b and whose flow properties are not to result in the contacts of the slip rings 4a and 4b floating up or in the frictional moment being inadmissibly increased.

An ultrasonic converter 7 is carried non-rotatably with respect to the shaft 6 on the free end of the shaft 6, which is outside the internal housing 3. When the motor 1 is activated the shaft 6 is caused to rotate about its longitudinal axis by way of the transmission 2, whereby the ultrasonic converter 7 is also correspondingly driven in rotation.

The above-described components are disposed in a tubular external housing 8. As FIG. 1 shows the wall of the external housing 8 is thicker in the region of the motor 1 and the transmission 2 than in the region of the internal housing 3 and the ultrasonic converter 7. In that way, as can be seen from FIG. 1, a step is formed in the region of the end of the transmission 2, which is towards the internal housing 3, at the inside wall of the external housing 8. The step is adjoined by a portion of a larger internal diameter in which the internal housing 3 is disposed. In this arrangement the internal housing 3 bears with its external peripheral surface against the surface of the internal wall of the external housing 8. At its end which is towards the transmission 2 the internal housing 3 has an inwardly protruding annular projection which is in engagement with the adjacent end of the casing of the transmission 2 and forms an axial holder.

At its free end—which is at the right in FIG. 1—the external housing 8 is closed so that there it forms a compartment which is closed by the sealing ring 5 with respect to the interior of the internal housing 3 and with respect to the surrounding environment in which the rotating ultrasonic converter 7 is arranged. That compartment in the housing 8 is preferably filled with a medium which serves for acoustic coupling of the ultrasonic converter 7 and which is necessary in particular for adaptation of the acoustic wave resistance of the ultrasonic converter 7, the external housing 8 and the human tissue.

The drive 1, the transmission 2, the slip rings 4a and 4b, the shaft 6 and the ultrasonic converter 7 which are all disposed in the external housing 8 form together with the latter a structural unit which, with its proximal end—at the left in FIG. 1—can be removably secured to a catheter (not shown in the Figures).

Figure 2:
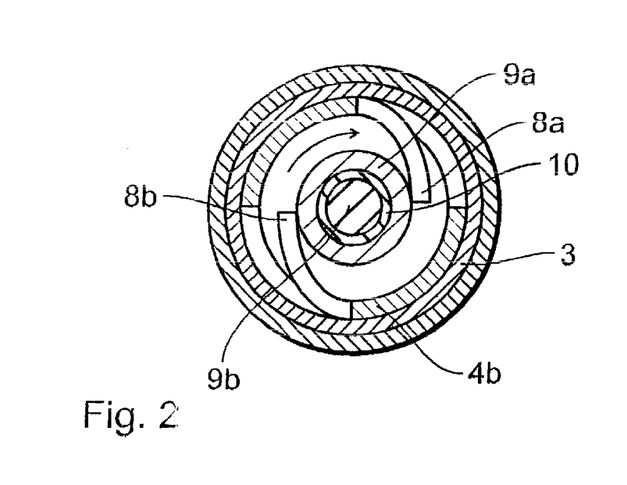
FIG. 2 is a section through a first embodiment of a slip ring arrangement disposed in the distal end, taken along line A—A in FIG. 1.

The cross-sectional view in FIG. 2 shows the structure of the slip ring 4b, in which respect the slip ring 4a in the illustrated embodiment is of the same structure. Accordingly the slip rings each have a cylindrical carrier which bears with its outside peripheral surface in surface contact with the inside wall surface of the internal housing 3. Cut out of the cylindrical carrier are inwardly curved contact springs 8a and 8b which are integrally connected with their one end to the cylindrical carrier and with their other end bear approximately tangentially against the periphery of the shaft 6. As illustrated in FIG. 2, the illustrated embodiment has two oppositely disposed contact springs 8a, 8b for each slip ring. It will be appreciated however that it is also possible to provide a larger number of contact springs on the slip rings. In the view shown in FIG. 2 the contact springs 8a, 8b are curved through about 90°. Alternatively however they may also be of a rectilinear shape. Equally however it is also possible for the contact springs to be of a spiral configuration in order to increase the resulting spring travel. At any event the contact springs 8a, 8b are resiliently biased in a radial direction towards the shaft 6 in order to guarantee certain contacting. The contact springs 8a, 8b either comprise a spring wire provided with one or more layers of contact material, or they comprise a contact material of suitable elastic properties.

As FIG. 2 also shows the contacted shaft 6 comprises a casing 9a and a solid metal core 9b as well as an interposed insulating layer 10, with the arrangement being coaxial. As the contact springs 8a, 8b bear against portions of the casing 9a, they form counterpart contacts in relation to the contact springs 8a, 8b. According to the number of slip rings 4a and 4b the casing 9a of the shaft 6 is divided into metallically conductive peripheral portions which are separated from each other by insulating portions, although this is not specifically shown in greater detail in the Figures.

Figure 3:
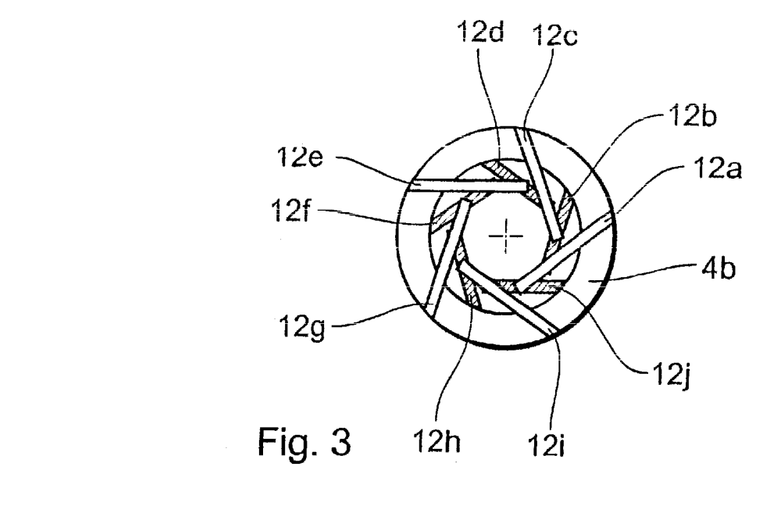
FIG. 3 is a section through a second embodiment of a slip ring arrangement disposed in the distal end, taken along line A—A in FIG. 1, wherein however the external housing, the internal housing and the shaft are omitted.

FIG. 3 is a view corresponding to FIG. 2 showing an alternative configuration of the contact arrangement, with the external housing 8, the internal housing 3 and the shaft 6 being omitted for reasons of improved clarity of the drawings. In this embodiment the illustrated slip ring 4b is in the form of a metal carrier on which contact portions 12a through 12j are arranged. In the embodiment illustrated in FIG. 3 there are ten contact portions 12a through 12j which are of a rectilinear configuration, with the ends thereof bearing tangentially against the periphery of the shaft 6 which is not shown in FIG. 3. The structure of the shaft 6 in this second embodiment is the same as in the first embodiment shown in FIG. 2. The contact portions 12a through 12j are in the form of spring elements and can comprise the same material as the contact springs 8a, 8b of the first embodiment.

The ultrasonic converter 7 is electrically connected by way of the above-described sliding contacts 4a and 4b to a signal processing unit (not shown) which is usually an external piece of equipment.

In that case the ultrasonic converter 7 is connected to the metallic peripheral portions of the casing 9a of the shaft 6 by conductors which are passed within the shaft, which is not specifically shown in detail in the Figures. This may involve individual wires which are insulated relative to each other. Alternatively or in addition the conductors may also be provided on the insulating layer 10. The casing 9a of the shaft 6 can also be used as a conductor. Wires which are also not shown in the Figures are passed from the cylindrical carriers of the slip rings 4a, 4b along the internal wall of the external housing 8 to the catheter which is not shown in the Figures and from there to the signal processing unit.

Material affording a high level of conductivity and in particular a high level of surface conductivity, and/or a low level of sliding friction, should be used for the contact springs 8a, 8b and/or for the associated electrically conductive peripheral portions of the casing 9a of the shaft 6. In particular noble metals, alloys thereof or sintered materials are suitable for that purpose. The contact springs 8a, 8b can also serve as radial guidance for the shaft 6. The sealing ring 5 also serves as an additional radial mounting. Nonetheless if necessary it is also possible to provide further radial and possibly axial thrust mountings which are not shown in the Figures.

Figure 4:
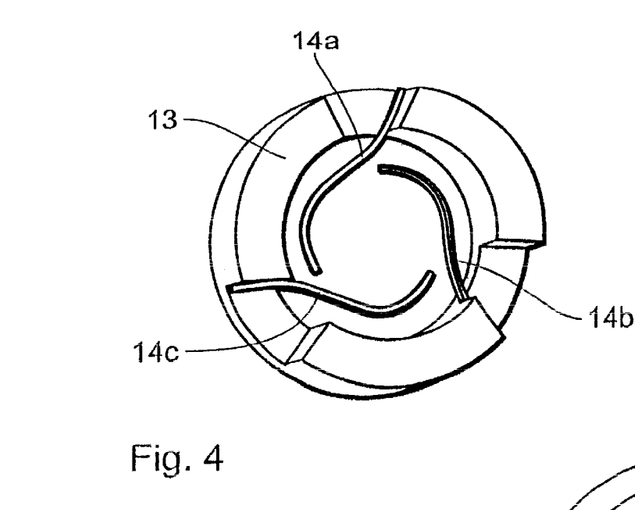
FIGS. 4–8 show alternative slip ring arrangements as perspective views without the external housing, the internal housing and the shaft together with first contact elements.
Figure 5:
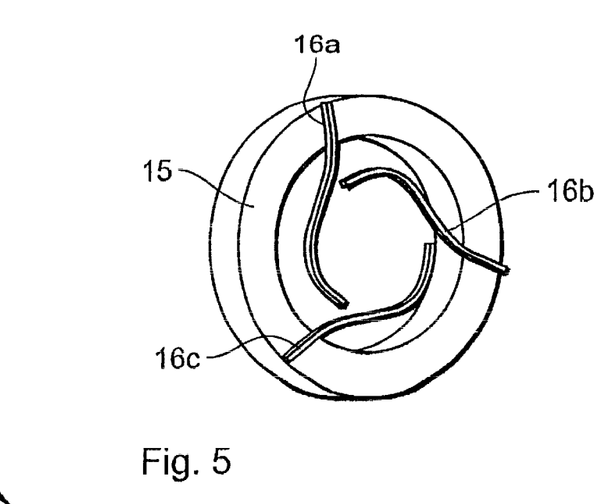

FIGS. 4 and 5 show two further alternative embodiments which can be used as an alternative to the slip rings 4a and 4b in FIG. 1. The slip rings shown in FIGS. 4 and 5 differ by virtue of the configuration of the respective cylindrical carriers 13 and 15. While the contact springs 14a through 14c in FIG. 4 are inserted into recesses in the cylindrical carrier 13 the contact springs 16a through 16c in FIG. 5 are fitted on a face of the carrier 15. Otherwise the contact springs 14a through 14c and 16a through 16c are essentially the same. The arrangements each have three contact springs which are equidistantly arranged in the radial direction and which are so shaped at their one end that they touch a cylindrical first contact element (not shown in FIGS. 4 and 5), if possible over the full periphery thereof. That results in surface contact between the first contact element and the contact springs 14 and 16 respectively. The first contact element can have a peripheral groove into which the contact springs 14 and 16 engage. That also affords axial fixing for the first contact element with respect to the second contact element which is formed by the carrier 13 or 15 respectively and the contact springs 14 or 16 respectively, that axial fixing action serves to provide axial support.

Figure 6:
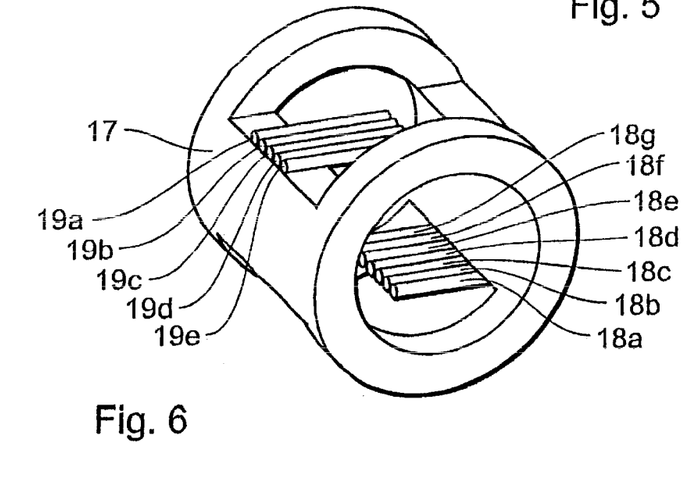

FIG. 6 shows an alternative slip ring comprising a cylindrical carrier 17 which admittedly has tangential openings arranged centrally in the longitudinal direction of the carrier and in which are arranged on one side seven straight contact springs 18a through 18g of round cross-section, which are all oriented tangentially and disposed in directly mutually adjacent relationship. On the other side there are five straight and tangentially oriented contact springs 19a through 19e of round cross-section, which are also in directly mutually adjacent relationship. In this case, each individual ones of the contact springs 18a through 18g and 19a through 19e is provided for point contact with a first contact element, but the plurality of contact springs affords reliable electrical contact.

Figure 7:
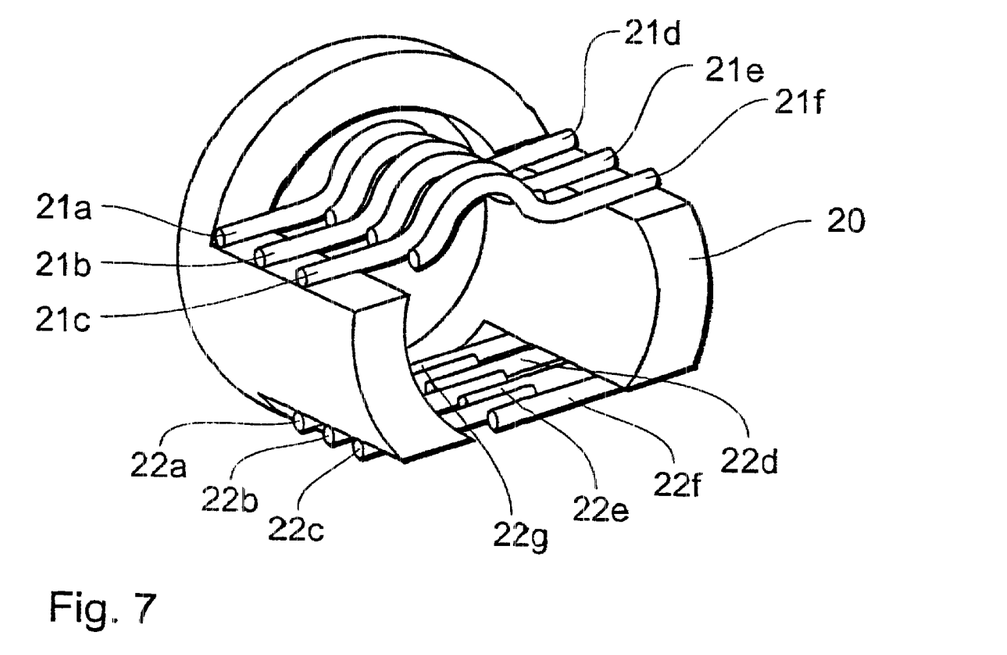

FIG. 7 shows a further alternative for a slip ring comprising a carrier 20 which is based on a cylindrical carrier having two tangential openings extending to an end face, similarly to the carrier shown in FIG. 6. The openings are of different depths so that the surfaces provided for fixing the contact springs 21a through 21j and 22a through 22g respectively are at a different spacing in relation to the longitudinal axis of a first contact element which is not shown in FIG. 7. That different spacing of the fixing surfaces for the contact springs 21a through 21j and 22a through 22g respectively is compensated by the shape of the contact springs. The contact springs 22a through 22g are straight and secured in mutually opposite relationship to the two fixing surfaces of that opening which is shown at the bottom in FIG. 7. The contact springs 21a through 21j are also fixed in opposite relationship to the fixing surfaces of the opening which is shown at the top in FIG. 7. The inwardly projecting ends of the contact springs 21a through 21j are curved in an arcuate configuration in such a way that the arc faces outwardly and permits line contact with a first contact element, for each contact spring 21a through 21j. The difference in depth of the two openings is compensated by the respective arcuate portion of each contact spring 21a through 21j.

Figure 8:
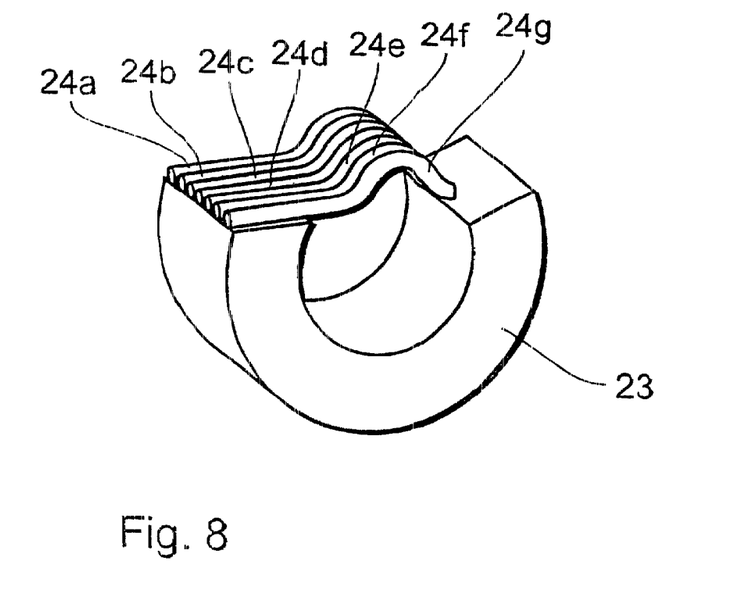

Finally FIG. 8 shows a slip ring whose carrier 23 is in the form of a plain bearing ring which is open on one side. Provided on the open side of the plain bearing ring 23 are a total of seven contact springs 24a through 24g which serve for contacting a first contact element which is mounted in the plain bearing ring 23. For that purpose they are provided at their free end with outwardly facing arguate portions which permit line or at least two-point contact between each contact spring and the first contact element. In contrast to the other illustrated variants, the variant of a slip ring as shown in FIG. 8 does not involve resilient radial support of the first contact element but fixed support in the manner of a plain bearing, by virtue of the opened plain bearing ring 23.

Figure 9:
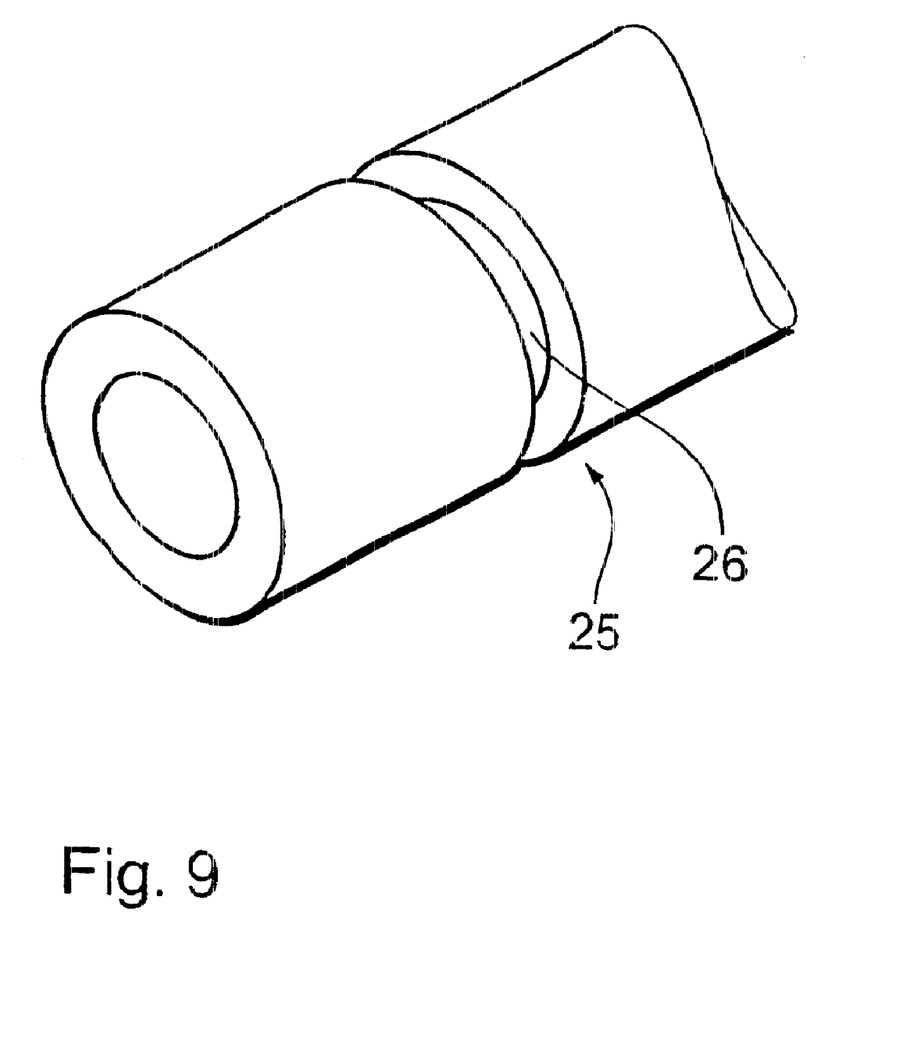
FIG. 9 shows a perspective view of a first contact element.

FIG. 9 shows a first contact element 25 having a peripheral groove 26 which, together with one or more second contact elements engaging thereinto, forms an axial mounting, possibly also a radial mounting.

Finally it should also be mentioned at this point that the illustrated ultrasonic converter can optionally also comprise a plurality of acoustically active segments of variable arrangement and shape, whose orientation can be axial and/or radial, wherein the contacting means can then be of such a configuration that current paths which are always at the same electrical potential can be combined together and contacted by way of a common sliding contact. Alternatively it is also possible to provide a corresponding plurality of ultrasonic converters.

What is claimed is:

1. An instrument for medical purposes, comprising:
   a housing, having a distal end, which can be introduced into an animal or human body, a movably mounted electromagnetic or acoustic transducer unit arranged in the housing for producing electromagnetic or acoustic waves and
   a drive for driving the transducer unit, wherein the transducer unit is connected to at least one first contact element and at least one second contact element is arranged on the housing for sliding contact with the first contact element,
   characterized in that the first and second contact elements jointly form an at least radial mounting for the transducer unit and are arranged in a region of the distal end of the housing.

2. The instrument of claim 1, wherein at least one of the respective contact elements is elastically mounted.

3. The instrument of claim 2, wherein more than one second contact element is provided for mounting the transducer unit.

4. The instrument of claim 3, wherein at least one of the second contact elements is adapted for point and/or line contact with at least one first contact element.

5. The instrument of claim 4, wherein at least one said first and at least one said second contact element jointly form an axial mounting for the transducer unit.

6. The instrument of claim 5, wherein the first contact element has a peripheral groove into which engages the second contact element.

7. The instrument of claim 6, wherein the transducer unit is disposed on a rotating and/or linearly oscillating shaft which is driven by the drive and on which the first contact element is arranged.

8. The instrument of claim 7, wherein a plurality of conductors that connect the first contact element to the transducer unit are arranged within the shaft.

9. The instrument of claim 8, wherein the shaft is hollow and the conductors are mutually insulated wires.

10. The instrument of claim 8, wherein the shaft is a hollow shaft whose internal wall has an insulating layer on which the conductors are arranged.

11. The instrument of claim 8, wherein the shaft has a plurality of coaxial portions which are annular in cross-section and which are insulated from each other and which form the conductors.

12. The instrument of claim 8, wherein the shaft comprises the plurality of conductors.

13. The instrument of claim 7, wherein the second contact element is a spring.

14. The instrument of claim 13, wherein the first contact element is an annular portion surrounding the shaft and the second contact element contacts the first contact element tangentially.

15. The instrument of claim 10, wherein the second contact element is a rectilinear spring plate.

16. The instrument of claim 13, wherein the second contact element is a curved spring plate.

17. The instrument of claim 13, wherein the second contact element is a coil spring surrounding the shaft.

18. The instrument of claim 1, wherein more than one second contact element is provided for mounting the transducer unit.

19. The instrument of claim 18, wherein at least one of the second contact elements is adapted for point and/or line contact with at least one first contact element.

20. The instrument of claim 1, wherein at least one said first and at least one said second contact element jointly form an axial mounting for the transducer unit.

21. The instrument of claim 20, wherein the first contact element has a peripheral groove into which engages the second contact element.

22. The instrument of claim 21, wherein the transducer unit is disposed on a rotating and/or linearly oscillating shaft which is driven by the drive and on which the first contact element is arranged.

23. The instrument of claim 22, wherein a plurality of conductors that connect the first contact element to the transducer unit are arranged within the shaft.

24. The instrument of claim 23, wherein the shaft is hollow and the conductors are mutually insulated wires.

25. The instrument of claim 23, wherein the shaft is a hollow shaft whose internal wall has an insulating layer on which the conductors are arranged.

26. The instrument of claim 23, wherein the shaft has a plurality of coaxial portions which are annular in cross-section and which are insulated from each other and which form the conductors.

27. The instrument of claim 23, wherein the shaft comprises the plurality of conductors.

28. The instrument of claim 22, wherein the second contact element is a spring.

29. The instrument of claim 28, wherein the first contact element is an annular portion surrounding the shaft and the second contact element contacts the first contact element tangentially.

30. The instrument of claim 28, wherein the second contact element is a rectilinear spring plate.

31. The instrument of claim 28, wherein the second contact element is a curved spring plate.

32. The instrument of claim 28, wherein the second contact element is a coil spring surrounding the shaft.

33. The instrument of claim 20, wherein at least one said first and at least one said second contact element jointly form an axial mounting for the transducer unit.

34. The instrument of claim 33, wherein the first contact element has a peripheral groove into which engages the second contact element.

35. The instrument of claim 1, wherein the transducer unit has at least one ultrasonic converter, characterized in that the said at least one ultrasonic converter is arranged in a housing portion which is sealed off with respect to the rest of the housing and contains a fluid for acoustic coupling purposes.

36. The instrument of claim 34, wherein the transducer unit is disposed on a rotating and/or linearly oscillating shaft which is driven by the drive and on which the first contact element is arranged.

37. The instrument of claim 36, wherein a plurality of conductors that connect the first contact element to the transducer unit are arranged within the shaft.

38. The instrument of claim 37, wherein the shaft is hollow and the conductors are mutually insulated wires.

39. The instrument of claim 37, wherein the shaft is a hollow shaft whose internal wall has an insulating layer on which the conductors are arranged.

40. The instrument of claim 37, wherein the shaft has a plurality of coaxial portions which are annular in cross-section and which are insulated from each other and which form the conductors.

41. The instrument of claim 37, wherein the shaft comprises the plurality of conductors.

42. The instrument of claim 36, wherein the second contact element is a spring.

43. The instrument of claim 42, wherein the first contact element is an annular portion surrounding the shaft and the second contact element contacts the first contact element tangentially.

44. The instrument of claim 42, wherein the second contact element is a rectilinear spring plate.

45. The instrument of claim 42, wherein the second contact element is a curved spring plate.

46. The instrument of claim 42, wherein the second contact element is a coil spring surrounding the shaft.

47. The instrument of claim 1, wherein the transducer unit is disposed on a rotating and/or linearly oscillating shaft which is driven by the drive and on which the first contact element is arranged.

48. The instrument as set forth in claim 47 characterized in that a plurality of conductors that connect the first contact element to the transducer unit are arranged within the shaft.

49. The instrument as set forth in claim 48 characterized in that the shaft is hollow and the conductors are mutually insulated wires.

50. The instrument of claim 48, wherein the shaft is a hollow shaft whose internal wall has an insulating layer on which the conductors are arranged.

51. The instrument as set forth in claim 48 the shaft has a plurality of coaxial portions which are annular in cross-section and which are insulated from each other and which form the conductors.

52. The instrument of claim 48, wherein the shaft comprises the plurality of conductors.

53. The instrument of claim 47, wherein the second contact element is a spring.

54. The instrument of claim 53, wherein the first contact element is an annular portion surrounding the shaft and the second contact element contacts the first contact element tangentially.

55. The instrument of claim 53, wherein the second contact element is a rectilinear spring plate.

56. The instrument of claim 53, wherein the second contact element is a curved spring plate.

57. The instrument of claim 53, wherein the second contact element is a coil spring surrounding the shaft.

58. The instrument of claim 1, wherein the second contact element is a spring.

59. The instrument as set forth in claim 58 characterized in that the first contact element is an annular portion surrounding the shaft and the second contact element contacts the first contact element tangentially.

60. The instrument of claim 58, wherein the second contact element is a rectilinear spring plate.

61. The instrument of claim 58, wherein the second contact element is a coil spring surrounding the shaft.

62. The instrument of claim 58, wherein the second contact element is a curved spring plate.

63. The instrument of claim 1, wherein the first and second contact elements are arranged jointly in a first housing portion which is sealed off with respect to the rest of the housing and contains gas or liquid.

64. The instrument of claim 1, wherein the drive is arranged in the housing adjacent to the transducer unit.

65. The instrument of claim 64, wherein the drive has a motor.

66. The instrument of claim 65, wherein the motor is a synchronous motor.

67. The instrument of claim 65, wherein the motor is an electrostatic motor.

68. The instrument of claim 65, wherein the motor is an electromagnetic motor.

69. The instrument of claim 65, wherein the motor is a piezoelectric motor.

70. The instrument of claim 65, wherein the motor is a magnetostrictive motor.

71. The instrument of claim 65, wherein the motor is a fluid motor.

72. The instrument of claim 1, wherein the drive has a transmission which has one or more stages and which has a uniform or non-uniform step-up action.

73. The instrument of claim 1, wherein the drive has a regulating means.

74. The instrument of claim 73 wherein the regulating means has an angle measurement converter.

75. The instrument of claim 1, wherein the transducer unit has a plurality of transducers which are oriented axially and/or radially in relation to a longitudinal axis of the housing.

76. The instrument of claim 75, wherein the plurality of transducers are ultrasonic converters.

77. The instrument of claim 1, further comprising a catheter having a distal end to which the housing is removably secured.

78. The instrument of claim 1, wherein the housing is a tube.

79. The instrument of claim 1, wherein the transducer unit is arranged in the distal end of the housing.

80. The instrument of claim 1, wherein the transducer unit produces ultrasonic waves.

* * * * *